(12) United States Patent
Maitra et al.

(10) Patent No.: US 8,568,695 B2
(45) Date of Patent: Oct. 29, 2013

(54) ORAL CARE COMPOSITION WITH SILICONE COMPOSITE

(75) Inventors: Prithwiraj Maitra, Randolph, NJ (US); Suman K. Chopra, Monroe, NJ (US); Harsh M. Trivedi, Somerset, NJ (US); Sayed Ibrahim, Somerset, NJ (US); Tao Xu, East Brunswick, NJ (US); Michael Prencipe, Princeton Junction, NJ (US)

(73) Assignee: Colgate-Palmolive Company, New York, NY (US)

( * ) Notice: Subject to any disclaimer, the term of this patent is extended or adjusted under 35 U.S.C. 154(b) by 519 days.

(21) Appl. No.: 11/739,393

(22) Filed: Apr. 24, 2007

(65) Prior Publication Data

US 2007/0253916 A1 Nov. 1, 2007

Related U.S. Application Data

(60) Provisional application No. 60/796,383, filed on May 1, 2006.

(51) Int. Cl.
*A61K 8/89* (2006.01)
*A61K 8/11* (2006.01)

(52) U.S. Cl.
USPC .......... 424/49; 424/70.12; 424/489; 424/490; 524/8

(58) Field of Classification Search
USPC ....................................................... 424/490
See application file for complete search history.

(56) References Cited

U.S. PATENT DOCUMENTS

| | | | |
|---|---|---|---|
| 2,667,473 A | 1/1954 | Morner et al. | |
| 2,938,017 A | 5/1960 | Grosser et al. | |
| 2,947,633 A | 8/1960 | Perry et al. | |
| 3,277,066 A | 10/1966 | Grosser et al. | |
| 3,306,881 A | 2/1967 | Grosser et al. | |
| 3,306,886 A | 2/1967 | Grosser et al. | |
| 3,759,880 A | 9/1973 | Hoffman et al. | |
| 3,992,562 A | 11/1976 | Denzinger et al. | |
| 4,013,825 A | 3/1977 | Denzinger et al. | |
| 4,038,257 A | 7/1977 | Suzuki et al. | |
| 4,136,250 A | 1/1979 | Mueller et al. | |
| 4,224,427 A | 9/1980 | Mueller et al. | |
| 4,250,322 A | 2/1981 | Efimov et al. | |
| 4,276,402 A | 6/1981 | Chromecek et al. | |
| 4,277,595 A | 7/1981 | Deichert et al. | |
| 4,341,889 A | 7/1982 | Deichert et al. | |
| 4,423,099 A | 12/1983 | Mueller et al. | |
| 4,543,398 A | 9/1985 | Bany et al. | |
| 4,564,514 A | 1/1986 | Druaz et al. | |
| 4,690,825 A * | 9/1987 | Won .............................. | 424/501 |
| 5,077,047 A | 12/1991 | Biss et al. | |
| 5,108,742 A | 4/1992 | Merianos | |
| 5,312,619 A | 5/1994 | Shih et al. | |
| 5,425,953 A | 6/1995 | Sintov et al. | |
| 5,712,358 A * | 1/1998 | Sojka ........................... | 526/323.2 |
| 5,718,886 A | 2/1998 | Pellico | |
| 5,766,574 A | 6/1998 | Christina-Beck et al. | |
| 5,776,435 A | 7/1998 | Gaffar et al. | |
| 5,945,032 A | 8/1999 | Breitenbach et al. | |
| 5,955,552 A | 9/1999 | Sojka | |
| 6,083,421 A | 7/2000 | Huang et al. | |
| 6,228,385 B1 | 5/2001 | Shick | |
| 6,290,933 B1 | 9/2001 | Durga et al. | |
| 6,348,211 B1 * | 2/2002 | Mantelle et al. ............... | 424/448 |
| 6,387,995 B1 | 5/2002 | Sojka | |
| 6,491,953 B1 | 12/2002 | Sojka et al. | |
| 6,514,484 B2 | 2/2003 | Rajaiah et al. | |
| 6,514,543 B2 | 2/2003 | Montgomery | |
| 6,555,020 B1 | 4/2003 | Chadwick et al. | |
| 6,685,921 B2 | 2/2004 | Lawlor | |
| 6,730,318 B2 * | 5/2004 | Quan et al. ..................... | 424/448 |
| 2003/0198604 A1 * | 10/2003 | Lawlor ........................... | 424/49 |
| 2003/0206874 A1 | 11/2003 | Doyle et al. | |
| 2003/0235549 A1 | 12/2003 | Singh et al. | |
| 2004/0086468 A1 | 5/2004 | Prosise et al. | |
| 2004/0241110 A1 | 12/2004 | Lee | |
| 2005/0036956 A1 | 2/2005 | Fei et al. | |
| 2005/0038181 A1 | 2/2005 | Chopra et al. | |
| 2006/0045854 A1 | 3/2006 | Zaidel et al. | |
| 2006/0147394 A1 | 7/2006 | Shastry et al. | |

FOREIGN PATENT DOCUMENTS

| | | |
|---|---|---|
| DE | 2365631 A1 | 10/1975 |
| EP | 0 417 971 | 3/1991 |
| GB | 1 205 325 | 9/1970 |
| JP | 60233110 A2 | 11/1985 |
| JP | 61009424 A | 1/1986 |
| JP | 61030566 A | 2/1986 |
| WO | WO 91/07184 | 5/1991 |
| WO | WO00/41528 * | 7/2000 |
| WO | WO 01/51012 | 7/2001 |
| WO | WO 2005/070378 | 8/2005 |
| WO | WO 2005/097053 | 10/2005 |
| WO | WO 2006/073822 A | 7/2006 |
| WO | WO 2006/026424 | 8/2006 |

OTHER PUBLICATIONS

Advanced Polymer Systems-Asset Purchase Agreeement, 1996, pp. 1-11, www.techagreements.com.*
International Specialty Products, "Applications—Toothpaste and Mouthwash," SP Polymers for Oral Care, (2003) 10 pps.
International Specialty Products, "Product and Applications Guide," ISP Polymers for Oral Care, (2003) 19 pps.
Spindler et al., "Poly-Pore Microparticle Delivery System, A Multifunctional Delivery System for Personal Care Products," Cosmetics and Toiletries Manufacture Worldwide,2002.
Prosecution History From U.S. Appl. No. 11/285,871.
Search Report and Written Opinion from corresponding PCT Application No. PCT/US2007/067300.

* cited by examiner

*Primary Examiner* — Frederick Krass
*Assistant Examiner* — Michael P Cohen
(74) *Attorney, Agent, or Firm* — Howard C. Lee

(57) ABSTRACT

A composite comprising a silicone compound sorbed onto a porous cross-linked polymer. This composition can be included in an oral care composition and inhibit bacterial adhesion on an oral surface.

20 Claims, No Drawings

ORAL CARE COMPOSITION WITH SILICONE COMPOSITE

CROSS REFERENCE TO RELATED APPLICATION

This application claims the benefit of priority to U.S. Provisional Patent Application Ser. No. 60/796,383, filed on 1 May 2006, which is incorporated herein by reference.

BACKGROUND OF THE INVENTION

Dental plaque or plaque bio-film is a soft deposit that forms on surfaces of the oral cavity, such as tissue and teeth, and comprises a complex mixture of an accumulation of bacteria and salivary as well as food by-products, starch, proteins and proteinacious material. Thus, inhibiting the growth of bio-film not only involves dispersing the accumulation of existing proteinacious materials, but also requires prohibiting and minimizing their reattachment to the tooth surface. Plaque adheres tenaciously at the points of irregularity or discontinuity (e.g., on rough calculus surfaces, at the gum line, on tongue surface and within crevices, and the like). Besides being unsightly, plaque is implicated in the occurrence of gingivitis and other forms of periodontal disease.

Bacteria thrive on the tongue. For the most part, the bacteria are a part of a protective bio-film that essentially renders them resistant to most treatments. Few people clean their tongue after brushing, even though it's been shown that as much as 50 percent of the mouth's bacteria can be found here. Additionally, for many people, brushing or scraping the tongue is difficult because of the gag reflex. Therefore, cleaning the tongue non-mechanically is highly desirable for those who are unable to do so with a mechanical device.

A wide variety of agents have been suggested in the art to retard plaque formation and the oral infections and dental disease associated with plaque formation. In spite of the extensive amount of products related to antibacterial dentifrice and related oral treatment compositions, there is still a need for a product with enhanced bacteria anti-attachment properties.

BRIEF SUMMARY OF THE INVENTION

A composite comprising a silicone compound sorbed onto a porous cross-linked polymer.

DETAILED DESCRIPTION OF THE INVENTION

As used throughout, ranges are used as a shorthand for describing each and every value that is within the range. Any value within the range can be selected as the terminus of the range.

The present invention provides oral care compositions and methods for administration or application to, or use with, a human or other animal subject. The oral care compositions deliver silicone compounds, such as silicon adhesives and silicone fluid, to surfaces of an oral cavity. In various embodiments, the compositions provide bacterial anti-attachment, or anti-adhesion properties.

As referred to herein, an "oral care composition" is any composition that is suitable for administration or application to the oral cavity a human or animal subject for enhancing the health, hygiene or appearance of the subject, in certain embodiments providing such benefits as the prevention or treatment of a physiologic condition or disorder, the provision of sensory, decorative or cosmetic benefits, and combinations thereof.

The present invention encompasses oral care compositions containing an anti-adhesion/anti-attachment agent. Embodiments include providing a delivery system or composition for inhibiting bacterial adhesion on an oral surface using an anti-attachment agent releasing oral care composition. In various embodiments, the compositions comprise a silicone composite having a silicone compound and a porous cross-linked polymer mixed in an orally acceptable carrier.

In various embodiments, the present invention provides compositions comprising a silicone composite having one or more silicone compounds. In certain embodiments, the silicone composite is present in the oral care composition at a concentration of about 0.5% to about 99%, optionally in various embodiments at an amount of about 1% to about 50%, about 5% to about 30%, about 7% to about 20%, or about 8% to about 15%. The silicone composite may contain, for example, a silicone adhesive and a silicone fluid, as discussed in more detail below.

Silicone compounds useful for inclusion in the silicone composite contain, but are not limited to, silicone polymers, silicone adhesives, silicone gums, silicone waxes, silicone elastomers, silicone fluids, silicone resins, silicone powders, and mixtures thereof. If the composite comprises a silicone adhesive and a silicone fluid, the adhesive may be present in an amount of about 0.01% to about 99% by weight, about 1% to about 50%, about 5% to about 30% about 7% to about 20%, or about 8% to about 15% by weight of the total composition. The fluid may be present in an amount (by weight of the total composition) of about 0.01% to about 99%, 0.1% to about 1% or about 0.5% to about 0.7%.

In one embodiment, the silicone compound of the composite comprises an amine compatible silicone adhesive, or a pressure sensitive adhesive (PSA) composition, including those that are well known in the art. Generally, silicone based PSA's are produced by condensing a silicone resin and an organosiloxane such as a polydiorganosiloxane. Suitable silicone polymers include the copolymer product of mixing a silanol terminated polydiorganosiloxane such as polydimethyl siloxane with a silanol-containing silicone resin whereby the silanol groups of the polydiorganosiloxane undergo a condensation reaction with the silanol groups of the silicone resin so that the polydiorganosiloxane is lightly crosslinked by the silicone resin (that is, the polydiorganosiloxane chains are bonded together through the resin molecules to give chain branching and entanglement and/or a small amount of network character) to form the silicone pressure sensitive adhesive. A catalyst, for example an alkaline material such as ammonia, ammonium hydroxide or ammonium carbonate, can be mixed with the silanol-terminated polydiorganosiloxane and the silicone resin to promote this crosslinking reaction. By copolymerizing the silicone resin with the silanol terminated polydiorganosiloxane, the self adhering property and the cohesive properties of a soft elastomer matrix. Modifying the silicone resin to polydiorganosiloxane ratio of the pressure sensitive adhesive will modify the tackiness of the oral care composition. For example, PSAs are available from the Dow-Corning Corporation under the brand name BIO-PSA™.

Silicone gums useful herein include high molecular weight polydiorganosiloxanes having a viscosity, at 25° C., of about 500,000 cS up to about 50,000,000 cS. Such silicone gums include those polydiorganosiloxanes with a weight average molecular weight of greater than 500,000. The polysiloxane gums for use herein can be linear or cyclic, and branched or unbranched. Substituents may have any structure as long as the resulting polysiloxanes are hydrophobic, are neither irritating, toxic nor otherwise harmful when applied to the oral cavity, and are compatible with the other components of the composition. Specific examples of siloxane gums include polydimethylsiloxane, methylvinylsiloxane, copolymer, poly(dimethylsiloxane, diphenyl, methyvinylsiloxane) copolymer and mixtures thereof. Silicone gums include those commercially available and marketed by General Electric. Silicone waxes include cosmetic waxes and silky waxes.

Polysiloxane fluids useful herein include those with a viscosity, at 25° C., of about 1 cStk to about 1000 cS, or about 2 cS to about 500 cS, or about 20 cS to about 400 cS. Polysiloxane fluids for use herein can be linear or cyclic, and can be substituted with a wide variety of substituents (including as described above). In certain embodiments, substituents include methyl, ethyl and phenyl substituents. Suitable polysiloxane fluids include linear polysiloxane polymers such as dimethicone and other low viscosity analogues of the polysiloxane materials, in certain embodiments having a viscosity, at 25° C., of 200 cS or less and cyclomethicone, and other cyclic siloxanes having for example a viscosity, at 25° C., of 200 cS or less. Other fluids include polysiloxane polyether copolymers and hydroxy terminated polydimethyl-siloxane fluid (e.g., Dow Corning ST-DIMETHICONOL™ 40, Dow Corning SGM 36, SGM3). Commercial examples of materials that are suitable for use herein include DC200 series fluids marketed by Dow-Corning Corporation and the AK Fluid series marketed by Wacker-Chemie GmbH, München, Germany. High molecular silicone resins with a polysiloxane blend may also be used including powdered trimethylsiloxysilicate, for example, Dow Corning 593 fluid, Wacker Belsil TMS 803.

Suitable elastomeric silicone powders can be used having a particle size of about 1 to about 15 μm, for example dimethicone/vinyl dimethicone cross polymers. Additionally, in certain embodiments, non-ionic emulsions containing 30% dimethicone can be used.

The oral composition contain a porous cross-linked polymer. As referred to herein, a "porous cross-linked polymer" is a particulate polymer material which is operable to sorb a silicone compound. The term "sorb" refers to the "sorptive" (or "sorption") capability of the polymer particles to adsorb, absorb, complex, or otherwise retain a silicone compound. As used herein, "porous" refers to the presence of voids or interstices between cross-linked polymers that increases the overall surface area of the polymer beyond a solely perimeter measurement. Without limiting the mechanism, function or utility of present invention, it is understood in some embodiments that the composite comprises polymeric particulates having a non-smooth surface and an irregular polymeric matrix in which the silicone compound is retained. The chemical and physical characteristics of the particulate hinder the release of the silicone compound from the polymer particulates, and in some embodiments provides sustained release of the silicone compound. In various embodiments, the polymer comprises porous particulates having a BET pore volume (Brunauer, Emmett and Teller method) of about 0.05 to about 0.3 cc/g, optionally about 0.1 to about 0.2 cc/g, optionally about 0.14 to about 0.16 cc/g. In one embodiment, the silicone composite comprises a silicone compound at an amount of about 50% to about 95%, about 70% to about 95%, or about 70% to about 90% by weight of the silicone composite.

In one embodiment, the cross-linked polymer is the polymerization product of at least one, and in other embodiments at least two, monomers having at least two unsaturated bonds (hereinafter referred to as "polyunsaturated" monomers), the monomers being polymerized including no more than about 40% by weight, and in other embodiments less than about 9% by weight, total monomer weight of monounsaturated co-monomers. The polyunsaturated monomers are selected from polyacrylates, polymethacrylates, polyitaconates and mixtures thereof. Included are poly-acrylates, -methacrylates, or -itaconates of: ethylene glycol, propylene glycol; di-, tri-, tetra-, or poly-ethylene glycol and propylene glycol; trimethylol propane, glycerin, erythritol, xylitol, pentaerythritol, dipentaerythritol, sorbitol, mannitol, glucose, sucrose, cellulose, hydroxyl cellulose, methyl cellulose, 1,2 or 1,3 propanediol, 1,3 or 1,4 butanediol, 1,6 hexanediol, 1,8 octanediol, cycloiexanediol, cyclohexanetriol, and mixtures thereof. Similarly, bis(acrylamido or methacrylamido) compounds can be used. These compounds are, for example, methylene bis(acryl or methacryl)amide, 1,2 dihydroxy ethylene bis(acryl or methacryl)amide, hexamethylene bis(acryl or methacryl)amide. In one embodiment, the polyunsaturated monomer is polymethacrylate.

Another group of useful monomers include di or poly vinyl esters, such as divinyl propylene urea, divinyl-oxalate, -malonate, -succinate, -glutamate. -adipate, -sebacate, -maleate, -fumerate, -citraconate, and -mesaconate. Other suitable polyunsaturated monomers include divinyl benzene, divinyl toluene, diallyl tartrate, allyl pyruvate, allyl maleate, divinyl tartrate, triallyl melamine, N,N'-methylene bis acrylamide, glycerine dimethacryl ate, glycerine trimethacrylate, diallyl maleate, divinyl ether, diallyl monoethyleneglycol citrate, ethyleneglycol vinyl allyl citrate, allyl vinyl maleate, diallyl itaconate, ethyleneglycol diester of itaconic acid, divinyl sulfone, hexahydro 1,3,5-triacryltriazine. triallyl phosphite, diallyl ether of benzene phosphonic acid, maleic anhydride triethylene glycol polyester, polyallyl sucrose, polyallyl glucose, sucrose diacrylate, glucose dimethacrylate, pentaerythritol di-, tri- and tetra-acrylate or methacrylate, trimethylol propane di- and triacrylate or methacrylate, sorbitol dimethacrylate, 2-(1-aziridinyl)-ethyl methacrylate, tri-ethanolamine diacrylate or dimethacrylate, triethanolamine triacrylate or trimethacrylate, tartaric acid dimethacrylate, triethyleneglycol dimethacrylate, the dimethacrylate of bishydroxy ethylacetamide and mixtures thereof.

Other suitable polyethylenically unsaturated cross-linking monomers include ethylene glycol diacrylate, diallyl phthalate, trimethylolpropanetrimethacrylate, polyvinyl and polyallyl ethers of ethylene glycol, of glycerol, of pentaerythritol, of diethyleneglycol, of monothio- and dithio-derivatives of glycols, and of resorcinol; divinylketone, divinylsulfide, allyl acrylate, diallyl fumarate, diallyl succinate, diallyl carbonate, diallyl malonate, diallyl oxalate, diallyl adipate, diallyl sebacate, diallyl tartrate, diallyl silicate, triallyl tricarballylate, triallyl aconitrate, triallyl citrate, triallyl phosphate, divinyl naphthalene, divinylbenzene, trivinylbenzene; alkyldivinylbenzenes having from 1 to 4 alkyl groups of 1 to 2 carbon atoms substituted on the benzene nucleus; alkyltrivinylbenzenes having 1 to 3 alkyl groups of 1 to 2 carbon atoms substituted on the benzene nucleus; trivinylnaphthalenes, polyvinylanthracenes, and mixtures thereof. In addition, acryl or methracryl-encapped siloxanes and polysiloxanes, methacryloyl end-capped urethanes, urethane acrylates of polysiloxane alcohols and bisphenol A bis methacrylate and ethoxylated bisphenol A bis methacrylate also are suitable as polyunsaturated monomers.

Still another group of monomers is represented by di or poly vinyl ethers of ethylene, propylene, butylene, and the like, glycols, glycerine, penta erythritol, sorbitol, di or poly allyl compounds such as those based on glycols, glycerine, and the like, or combinations of vinyl allyl or vinyl acryloyl compounds such as vinyl methacrylate, vinyl acrylate, allyl methacrylate, allyl acrylate, methallyl methacrylate, or methallyl acrylate. In addition, aromatic, cycloaliphatic and heterocyclic compounds are suitable for this invention. These compounds include divinyl benzene, divinyl toluene, divinyl diphenyl, divinyl cyclohexane, trivinyl benzene, divinyl pyridine, and divinyl piperidine. Furthermore, divinyl ethylene or divinyl propylene urea and similar compounds may be used, e.g., as described in U.S. Pat. Nos. 3,759,880; 3,992,562; and 4,013,825. Acryloyl- or methacryloyl end-capped siloxane and polysiloxanes such as those described in U.S. Pat. No. 4,276,402 (equivalent to German Patent Publication No. 30 34 505); U.S. Pat. Nos. 4,341,889; and 4,277,595 (equivalent to French Patent 2,465,236) are suitable for this invention. Methacryloyl end-capped urethanes, such as those described in U.S. Pat. Nos. 4,224,427; 4,250,322; 4,423,099; and 4,038,257 (equivalent to German Patent Publication No. 25 42 314), German Patent Publications No. 23 65 631, Japanese Patent Publication Nos. 60-233,110; 61-009,424, and 61-030,566, and British Patent Publication No. 1,443,715, are suitable for this invention. Urethane acrylates of polysiloxane alcohols as described in U.S. Pat. Nos. 4,543,398 and 4,136,250 and bisphenol A bis methaerylate and ethoxylated bisphenol A bis methaerylate are also suitable monomers for this invention. Each of the above listed patents is incorporated herein by reference.

Monoethylenically unsaturated monomers are also suitable, in an amount up to about 40% by weight, and in other embodiments no more than about 9% by weight, based on the total weight of monomers, for preparing polymer micro-particles include ethylene, propylene, isobutylene, disobutylene, styrene, vinyl pyridine ethylvinylbenzene, vinyltoluene, and dicyclopentadiene; esters of acrylic and methacrylic acid, including the methyl, ethyl, propyl, isopropyl, butyl, sec-butyl, tert-butyl, amyl, hexyl, octyl, ethylhexyl, decyl, dodecyl, cyclohexyl, isobornyl, phenyl, benzyl, alkylphenyl, ethoxymethyl, ethoxyethyl, ethoxyproyl, propoxymethyl, propoxyethyl, propoxypropyl, ethoxyphenyl, ethoxybenzyl, and ethoxycyclohexyl esters; vinyl esters, including vinyl acetate, vinyl propionate, vinyl butyrate and vinyl laurate, vinyl ketones, including vinyl methyl ketone, vinyl ethyl ketone, vinyl isopropyl ketone, and methyl isopropenyl ketone, vinyl ethers, including vinyl methyl ether, vinyl ethyl ether, vinyl propyl ether, and vinyl isobutyl ether; and the like.

Other monounsaturated monomer materials which may be utilized in accordance with the present invention, in an amount up to about 40% by weight or less, in other embodiments no more than about 25% by weight, and in other embodiments no more than about 9% by weight, based on the total weight of monomers in the monomer solution, include hydroxy alkyl esters of alpha, beta-unsaturated carboxylic acids such as 2-hydroxy ethylacrylate or methacrylate, hydroxypropylacrylate or methacrylate and the like. Many derivatives of acrylic or methacrylic acid other than the esters mentioned are also suitable as starting monounsaturated monomer materials for use in forming the unsaturated polymer micro-particles of the present invention. These include, but are not limited to the following monomers: methacrylylglycolic acid, the monomethacrylates of glycol, glycerol, and of other polyhydric alcohols, the monomethacrylates of dialkylene glycols and polyalkylene glycols, and the like. The corresponding acrylates in each instance may be substituted for the methacrylates. Examples include the following: 2-hydroxyethyl acrylate or methacrylate, diethylene glycol acrylate or methacrylate, 2-hydroxypropyl hydroxypropyl acrylate or methacrylate, 3-hydroxypropyl acrylate or methacrylate, tetraethyleneglycol acrylate or methacrylate, pentaethyleneglycol acrylate or methacrylate, dipropyleneglycol acrylate or methacrylate, acrylamide, methacrylamide, diacetone acrylamide methylolacrylamide methylolmethacrylanide and any acrylate or methacrylate having one or more straight or branched chain alkyl groups of 1 to 30 carbon atoms, or in certain embodiments 5 to 18 carbon atoms, and the like. Other suitable examples include isobornyl methacrylate, phenoxyethyl methacrylate, isodecyl methacrylate, stearyl methacrylate, hydroxypropyl methacrylate, cyclonexyl methacrylate, dimethylaminoethyl methacrylate, t-butylaminoethyl methacrylate, 2-acrylamido propane sulfonic acid, 2-ethylexyl methacrylate, methyl methacrylate, ethyl methacrylate, butyl methacrylate, 2-hydroxyethyl methacrylate, tetrahydrofurfuryl methacrylate and methoxyethyl methacrylate.

Examples of monounsaturated monomers containing carboxylic acid groups as functional groups and suitable for use as starting materials in accordance with the invention include the following: acrylic acid, methacrylic acid, itaconic acid, aconitic acid, cinnamic acid, crotonic acid, mesaconic acid, maleic acid, fumaric acid and the like.

Partial esters of the above acids are also suitable as monosaturated monomers for use in accordance with the invention. Examples of such esters include the following: mono-2-hydroxypropyl aconitate, mono-2-hydroxyethyl maleate, mono-2-hydroxypropyl fumarate, mono-ethyl itaconate, monomethyl cellosolve ester of itaconic acid, monomethyl cellosolve ester of maleic acid, and the like.

Examples of suitable monounsaturated monomers containing amino groups as functional groups include the following: diethylaminoethyl acrylate or methacrylate, dimethylaminoethyl acrylate or methacrylate, monoethylaminoethyl acrylate or methacrylate, tertbutylaminoethyl methacrylate, para-amino styrene, ortho-amino styrene, 2-amino-4-vinyl toluene, piperidinoethyl methacrylate, morpholinoethyl methacrylate, 2-vinyl pyridine, 3-vinyl pyridine, 4-vinyl pyridine, 2-ethyl-5-vinyl pyridine, dimethyl aminopropyl acrylate and methacrylate, dimethylaminoethyl vinyl ether, dimethylaminoethyl vinyl sulfide, diethylaminoethyl vinyl ether, aminoethyl vinyl ether, 2-pyrrolidinoethyl methacrylate, 3-dimethylamino ethyl-2-hydroxy-propylacrylate or methacrylate, 2-aminoethyl acrylate or methacrylate, isopropyl methacrylamide, N-methyl acrylamide or methacrylamide, 2-hydroxyethyl acrylamide or methacrylamide, 1-methacryloyl-2-hydroxy-3-trimethyl ammonium chloride or sulfomethylate, 2-(1-aziridinyl)-ethyl methacrylate, and the like. Polyethylenically unsaturated monomers which ordinarily act as though they have only one unsaturated group, such as isoprene, butadiene and chloroprene, should not be calculated as part of the polyunsaturated monomer content, but as part of the monoethylenically unsaturated monomer content.

In one embodiment, two polymerized polyunsaturated monomers are used. Allyl methacrylates polymerized with ethylene glycol dimethacrylate are particularly suitable for trapping a silicone compound to form the silicone composite. In such an embodiment, the diunsaturated monomers also function as cross-linking agents. This specific polymerization product is a polymeric porous sphere that appears as a powder.

In one embodiment, the polymer particulates useful herein are made by a process comprising:
 a) dissolving at least one, and in other embodiments at least two, polyunsaturated monomers, and in some embodiments along with an effective amount of an organic polymerization initiator, in a water-immiscible silicone fluid solvent, to provide a monomer mixture;

b) slowly agitating the dissolved monomers and silicone solvent;

c) continuing slow agitation during polymerization of the monomers in the silicone fluid to produce microporous polymer micro-particles and agglomerates thereof; and d) separating the microporous polymer micro-particles and agglomerates from the silicone solvent to produce microporous, polymer micro-particles and aggregates in the form of spheres.

In various embodiments, the sphere aggregates and sphere agglomerates having a diameter of less than about 500 microns, in other embodiments less than about 100 microns, or in other embodiments less than about 80 microns.

Porous cross-linked polymers among those useful herein are disclosed in U.S. Pat. Nos. 5,955,552 and 6,387,995. Such polymers include those commercially available as: MICROSPONGE™ 5640, marketed by A.P. Pharma, Redwood City, Calif., U.S.A.; POLYTRAP™ 6603 and POLY-PORE™ 200 series, marketed by Amcol International Corp, Arlington Heights, Ill., U.S.A.; and DSPCS-12 series and SPCAT-12 series, marketed by Kobo Products, Inc., South Plainfield, N.J., U.S.A. Each of the above-listed patents is incorporated herein by reference.

The present invention provides compositions comprising an orally acceptable carrier or dentifrice vehicle. As used herein, an "orally acceptable carrier" refers to a material or combination of materials that are safe for use in the compositions of the present invention, commensurate with a reasonable benefit/risk ratio, with which the silicone composite may be associated while retaining significant efficacy. In certain embodiments, it is desired that the carrier not substantially reduce the efficacy of the silicone composite. Selection of specific carrier components is dependant on the desired product form, including dentifrices, rinses, gels, and paints. In various embodiments, the carrier is operable to sufficiently adhere the silicone composite against surfaces within the oral cavity to which the composition is administered, without concomitant use of a dental tray, mouthpiece, tape, or similar appliance. In various embodiments, the carrier is operable for use with a tape, tray, mouthpiece or similar appliance. Carriers may be either aqueous or non-aqueous phases. Aqueous phase carriers in certain embodiments contain a humectant therein. The humectant in certain embodiments is glycerin, sorbitol, xylitol, and/or propylene glycol having a weight average molecular weight of about 200 to about 1,000. The humectant concentration typically totals about 5% to about 70% of the oral composition. In various embodiments, the carrier is non-aqueous.

Materials among those that are useful in carriers include adhesion agents, thickening agents, viscosity modifiers, diluents, surfactants, foam modulators, humectants, pH modifying agents, mouth feel agents, flavorants, sweeteners, and other optional ingredients such as whitening agents, abrasives, anticaries agents, etc. as will be discussed below. It is understood that while general attributes of each of the above categories of materials may differ, there may be some common attributes and any given material may serve multiple purposes within two or more of such categories of materials. Generally, such carrier materials are selected for compatibility with the silicone composite and with other ingredients of the composition.

In various embodiments, the carrier comprises an adhesion agent. As referred to herein, an adhesion agent is a material or combination of materials that enhance the retention of the silicone composite on the oral cavity surface onto which the composition is applied. Such adhesion agents include adhesives, film forming materials, viscosity enhancers and combinations thereof. Such materials include hydrophilic organic polymers, hydrophobic organic polymers, silicone gums, silicas, and combinations thereof.

Hydrophilic organic polymers useful herein include polyethylene glycols, nonionic polymers of ethylene oxide, block copolymers of ethylene oxide and propylene oxide, carboxymethylene polymers, polyvinyl pyrrolidone (PVP) and mixtures thereof. Nonaqueous hydrophilic polymers useful in the practice of the present invention in certain embodiments provide a viscosity for the composition in the amount of about 10,000 mPas (cps) to 600,000 mPas (cps).

Hydrophilic polymers also include polymers of polyethylene glycols and ethylene oxide having the general formula: $HOCH_2(CH_2OCH_2)_nOH$, wherein n represents the average number of oxyethylene groups. Polyethylene glycols available from Dow Chemical (Midland, Mich.) are designated by number such as 200, 300, 400, 600, 2000 which represents the approximate weight average molecular weight of the polymer. Polyethylene glycols 200, 300, 400, and 600 are clear viscous liquids at room temperature, and are used in certain embodiments of the present invention.

Another hydrophilic polymer useful herein is comprised of a water soluble, nonionic block copolymer of ethylene oxide and propylene oxide of the formula: $HO(C_2H_4O)_a(C_3H_6O)_b(C_2H_4O)CH$. The block copolymer in certain embodiments is chosen (with respect to a, b and c) such that the ethylene oxide constituent comprises about 65 to about 75% by weight, of the copolymer molecule and the copolymer has a weight average molecular weight of about 2,000 to about 15,000, with the copolymer being present in oral care composition in such concentration that the composition is liquid at room temperature (23° C.).

A block copolymer useful herein is PLURAFLO™ L1220 of BASF Corporation, which has a weight average molecular weight of about 9,800. The hydrophilic poly(ethylene oxide) block averages about 65% by weight of the polymer.

Organic polymers useful as adhesion enhancing agents include hydrophilic polymers such as carbomers such as carboxymethylene polymers such as acrylic acid polymers, and acrylic acid copolymers. Carboxypolymethylene is a slightly acidic vinyl polymer with active carboxyl groups. A carboxypolymethylene is CARBOPOL™ 974 marketed by Noveon, Inc., Cleveland, Ohio, U.S.A..

Hydrophobic organic materials useful as adhesion enhancing agents in the practice of the present invention include hydrophobic materials such as waxes such as bees wax, mineral oil, mineral oil and polyethylene blends, petrolatum, white petrolatum, liquid paraffin, butane/ethylene/styrene hydrogenated copolymer) blends (VERSAGEL™ marketed by Penreco, Houston, Tex., U.S.A.), acrylate and vinyl acetate polymers and copolymers, polyethylene waxes, silicone polymers as discussed further herein and polyvinyl pyrrolidone/vinyl acetate copolymers. In embodiments of the present invention containing a hydrophobic polymer, they can be present in amounts of about 1 to about 85% weight of the composition.

Adhesions agents also include inorganic materials. Such inorganic materials include silicon polymers such as amorphous silica compounds which function as thickening agents (CAB-O-SIL™ fumed silica manufactured by Cabot Corporation, Boston, Mass., U.S.A.; and SYLOX™ 15 also known as SYLODENT™ 15, marketed by Davison Chemical Division of W.R. Grace & Co., Columbia, Md., U.S.A.).

Thickening agents among those useful herein include carboxyvinyl polymers, carrageenans (also known as Irish moss and more particularly iota-carrageenan), cellulosic polymers such as hydroxyethylcellulose, carboxymethylcellulose (carmellose) and salts thereof (e.g., carmellose sodium), natural gums such as karaya, xanthan, gum arabic and tragacanth, colloidal magnesium aluminum silicate, colloidal silica and the like. One or more thickening agents are optionally present in a total amount of about 0.01% to about 15%, for example about 0.1% to about 10% or about 0.2% to about 5% by weight of the composition.

Viscosity modifiers among those useful herein include mineral oil, petrolatum, clays and organomodified clays, silica and the like. In various embodiments, such viscosity modifiers are operable to inhibit settling or separation of ingredients or to promote redispersibility upon agitation of a liquid composition. One or more viscosity modifiers are optionally present in a total amount of about 0.01% to about 10%, for example about 0.1% to about 5%.

Diluents among those useful herein include materials or combinations of materials that are operable to solubilize and/or suspend other components of the composition. In various embodiments, diluents are operable to adjust the viscosity of the composition, optionally in conjunction with viscosity modifiers (as discussed herein) and other components of the composition. In various embodiments, the composition is non-aqueous, i.e., does not contain appreciable amounts of chemically-unbound water. Diluents include glycerin and anhydrous alcohol. Diluents are optionally present in the nonaqueous liquid whitening compositions of the present invention in amounts of about 0.1% to about 90%, optionally in various embodiments about 0.5% to about 70%, about 0.5% to about 50%, or about 0.5% to about 35%.

Various embodiments of the present invention optionally comprise a surface active agent, which may function as a surfactant, emulsifier, and/or foam modulator. Surface active agents, or surfactants are conventionally employed in a variety of oral care formulations, to provide solubilization, dispersion, emulsification and wetting of the other ingredients present, especially flavor oils. Surface active agents generally achieve increased prophylactic action, by thoroughly dispersing the active ingredient agents throughout the film, and in certain instances, through the oral cavity as the film dissolves. Further, surface active ingredients can improve the cosmetic appearance of the film composition. Suitable surface active and emulsifying agents are those which are reasonably stable throughout a wide pH range, including non-soap anionic, nonionic, zwitterionic and amphoteric organic synthetic detergents. In certain embodiments, one or more surfactants are present in the adhesive layer of the oral film composition of the present invention in amounts of about 0.01% to about 10%, about 0.1% to about 5%, or about 0.5% to about 2%.

Nonionic surfactants useful in the compositions of the present invention include compounds produced by the condensation of alkylene oxides (especially ethylene oxide) with an organic hydrophobic compound, which may be aliphatic or alkylaromatic in nature. One group of surfactants is known as "ethoxamers". These include condensation products of ethylene oxide with fatty acids, fatty alcohols, fatty amides, polyhydric alcohols, (e.g., sorbitan monostearate) and the like. "Polysorbates" is the name given to a class of nonionic surfactants prepared by ethoxylating the free hydroxyls of sorbitan-fatty acid esters. They are commercially available, for example as the TWEEN™ surfactants of ICI, US Inc. Non-limiting examples include Polysorbate 20 (polyoxyethylene 20 sorbitan monolaurate, TWEEN™ 20) and Polysorbate 80 (polyoxyethylene 20 sorbitan mono-oleate, TWEEN™ 80). In certain embodiments, polysorbates include those with about 20 to 60 moles of ethylene oxide per mole of sorbitan ester. Nonionic surfactants are optionally present in embodiments of this invention at amounts of about 0.01% to about 1%.

Other suitable nonionic surfactants include poly(oxyethylene)-poly(oxypropylene) block copolymers, especially triblock polymers of this type with two blocks of poly(oxyethylene) and one block of poly(oxypropylene). Such copolymers are known commercially by the non-proprietary name of poloxamers, the name being used in conjunction with a numeric suffix to designate the individual identification of each copolymer. Poloxamers may have varying contents of ethylene oxide and propylene oxide, leading to a wide range of chemical structures and molecular weights. In one embodiment, the poloxamer is poloxamer 407. It is widely available, for example under the trade name PLURONIC™ F127 of BASF Corporation.

Other non-limiting examples of suitable nonionic surfactants include products derived from the condensation of ethylene oxide with the reaction product of propylene oxide and ethylene diamine, long chain tertiary amine oxides, long chain tertiary phosphine oxides, long chain dialkyl sulfoxides and the like.

Still other surfactants useful in various embodiments of the present invention include zwitterionic synthetic surfactants. Certain of these can be broadly described as derivatives of aliphatic quaternary ammonium, phosphonium, and sulfonium compounds, in which the aliphatic radicals can be straight chain or branched, and where one of the aliphatic substituents contains from 8 to 18 carbon atoms and one contains an anionic water-solubilizing group, e.g., carboxy, sulfonate., sulfate, phosphate or phosphonate. One example of a suitable zwitterionic surfactant is 4-(N,N-di(2-hydroxyethyl)-N-octadecylammonio)-butane-1-carboxylate.

Other suitable zwitterionic surfactants include betaine surfactants, such as those disclosed in U.S. Pat. No. 5,180,577. Typical alkyldimethyl betaines include decyl betaine 2-(N-decyl-N,N-dimethylammonio)acetate, cocobetaine, myristyl betaine, palmityl betaine, lauryl betaine, cetyl betaine, stearyl betaine, and the like. The amidobetaines are exemplified by cocoamidoethyl betaine, cocoamidopropyl betaine, lauramidopropyl betaine and the like. Particularly useful betaine surfactants include cocoamidopropyl betaine and lauramido propyl betaine.

Suitable examples of anionic surfactants are water-soluble salts of higher fatty acid monoglyceride monosulfates. Such as the sodium salt of the monosulfated monoglyceride of hydrogenated coconut oil fatty acids, higher alkyl sulfates such as sodium lauryl sulfate (SLS), alkyl aryl sulfonates such as sodium dodecyl benzene sulfonate, higher alkyl sulfoacetates, higher fatty acid esters of 1,2-dihydroxy propane sulfonate, and the substantially saturated higher aliphatic acyl amides of lower aliphatic amino carboxylic acid compounds, such as those having 12 to 16 carbons in the fatty acid, alkyl or acyl radicals, and the like. Examples of the last mentioned amides are N-lauroyl sarcosine, and the sodium, potassium, and ethanolamine salts of N-lauroyl, N-myristoyl, or N-palmitoyl sarcosine which are in certain embodiments substantially free from soap or similar higher fatty acid material.

Foam modulators useful herein include materials operable to increase amount, thickness or stability of foam generated by the composition (e.g., dentifrice compositions) upon agitation. Any orally acceptable foam modulator can be used, including polyethylene glycols (PEGs), also known as polyoxyethylenes. High molecular weight PEGs are suitable, including those having a weight average molecular weight of about 200,000 to about 7,000,000, for example about 500,000 to about 5,000,000 or about 1,000,000 to about 2,500,000.

One or more PEGs are optionally present in a total amount of about 0.1% to about 10%, for example about 0.2% to about 5% or about 0.25% to about 2%.

Humectants useful herein include polyhydric alcohols such as glycerin, sorbitol, xylitol or low molecular weight PEGs. In various embodiments, humectants are operable to prevent hardening of paste or gel compositions upon exposure to air. In various embodiments humectants also function as sweeteners. One or more humectants are optionally present in a total amount of about 1% to about 50%, for example about 2% to about 25% or about 5% to about 15%.

pH modifying agents among those useful herein include acidifying agents to lower pH, basifying agents to raise pH and buffering agents to control pH within a desired range. For example, one or more compounds selected from acidifying, basifying and buffering agents can be included to provide a pH of about 2 to about 10, or in various embodiments about 2 to about 8, about 3 to about 9, about 4 to about 8, about 5 to about 7, about 6 to about 10, about 7 to about 9, etc. Any orally acceptable pH modifying agent can be used, including without limitation carboxylic, phosphoric and sulfonic acids, acid salts (e.g., monosodium citrate, disodium citrate, monosodium malate, etc.), alkali metal hydroxides such as sodium hydroxide, carbonates such as sodium carbonate, bicarbonates, sesquicarbonates, borates, silicates, phosphates (e.g., monosodium phosphate, trisodium phosphate, pyrophosphate salts, etc.), imidazole and the like. One or more pH modifying agents are optionally present in a total amount effective to maintain the composition in an orally acceptable pH range.

Mouth-feel agents include materials which impart a desirable texture or other feeling during use of the composition. Such agents include bicarbonate salts, which in various embodiments impart a "clean feel" to teeth and gums due to effervescence and release of carbon dioxide. Any orally acceptable bicarbonate can be used, including without limitation alkali metal bicarbonates such as sodium and potassium bicarbonates, ammonium bicarbonate and the like. One or more bicarbonate salts are optionally present in a total amount of 0.1% to about 50%, for example about 1% to about 20%.

Flavorants among those useful herein include any material or mixture of materials operable to enhance the taste of the composition. Any orally acceptable natural or synthetic flavorant can be used, such as flavoring oils, flavoring aldehydes, esters, alcohols, similar materials, and combinations thereof. These flavoring agents can be synthetic flavor oils and flavoring aromatics, and/or oils, oleo resins and extracts derived from plants, leaves, flowers, fruits and so forth, and combinations thereof. In certain embodiments, the flavoring agent comprises an essential oil, extract or flavoring aldehyde, ketone, ester or alcohol that imparts a flavor selected from the group consisting of spearmint, peppermint, wintergreen, sassafras, clove, sage, eucalyptus, marjoram, cinnamon, lemon, lime, grapefruit, orange, apple, pear, peach, strawberry, cherry, apricot, watermelon, banana, coffee, cocoa, cola, miswak, menthol, carvone, anethole and combinations thereof. Representative flavor oils include: spearmint oil, cinnamon oil, peppermint oil, clove oil, bay oil, thyme oil, cedar leaf oil, oil of nutmeg, oil of sage, and oil of bitter almonds. Also useful are artificial, natural or synthetic fruit flavors such as vanilla, chocolate, coffee, cocoa and citrus oil, including lemon, orange, grape, lime and grapefruit and fruit essences including apple, pear, peach, strawberry, raspberry, cherry, plum, pineapple, apricot and so forth. These flavorings can be used individually or in combination.

Commonly used flavors include mints such as peppermint, wintergreen, spearmint, birch, anise and such fruit flavors, as cherry, lemon-lime, orange, grape, artificial vanilla, cinnamon derivatives, and others, whether employed individually or in combination. Flavorings such as aldehydes and esters including cinnamyl acetate, cinnamaldehyde, citral, diethylacetal, dihydrocarvyl acetate, eugenyl formate, p-methylanisole, and so forth can also be used. Further examples of aldehyde flavorings include, but are not limited to acetaldehyde (apple); benzaldehyde (cherry, almond); cinnamic aldehyde (cinnamon); citral, i.e., alpha citral (lemon, lime); neral, i.e., beta citral (lemon, lime); decanal (orange, lemon); ethyl vanillin (vanilla, cream); heliotropine, i.e., piperonal (vanilla, cream); vanillin (vanilla, cream); alpha-amyl cinnamaldehyde (spicy fruity flavors); butyraldehyde (butter, cheese); valeraldehyde (butter, cheese); citronellal (modifies, many types); decanal (citrus fruits); aldehyde C-8 (citrus fruits); aldehyde C-9 (citrus fruits); aldehyde C-12 (citrus fruits); 2-ethyl butyraldehyde (berry fruits); hexenal, i.e., trans-2 (berry fruits); tolyl aldehyde (cherry, almond); veratraldehyde (vanilla); 2,6-dimethyl-5-heptenal, i.e., melonal (melon); 2-6-dimethyloctanal (green fruit); and 2-dodecenal (citrus, mandarin); cherry; grape; mixtures thereof; and the like. Generally the flavoring can be incorporated in the present invention in an amounts of about 1% to about 10% by weight. In other embodiments, the flavoring agent is present about 2% to about 8%. In one embodiment, the flavoring agent is crystal blanc flavor, present at about 1%.

Sweeteners among those useful herein include orally acceptable natural or artificial, nutritive or non-nutritive sweeteners. Such sweeteners include dextrose, polydextrose, sucrose, maltose, dextrin, dried invert sugar, mannose, xylose, ribose, fructose, levulose, galactose, corn syrup (including high fructose corn syrup and corn syrup solids), partially hydrolyzed starch, hydrogenated starch hydrolysate, sorbitol, mannitol, xylitol, maltitol, isomalt, aspartame, neotame, saccharin and salts thereof, sucralose, dipeptide-based intense sweeteners, cyclamates, dihydrochalcones and the like. In various embodiments, sodium saccharin is used as the sweetener. One or more sweeteners are optionally present in a total amount depending strongly on the particular sweetener(s) selected, but typically at amounts of about 0.005% to about 5%, optionally about 0.01% to about 1%.

Colorants among those useful herein include pigments, dyes, lakes and agents imparting a particular luster or reflectivity such as pearling agents. In various embodiments, colorants are operable to provide a white or light-colored coating on a dental surface, to act as an indicator of locations on a dental surface that have been effectively contacted by the composition, and/or to modify appearance, in particular color and/or opacity, of the composition to enhance attractiveness to the consumer. Any orally acceptable colorant can be used, including talc, mica, magnesium carbonate, calcium carbonate, magnesium silicate, magnesium aluminum silicate, silica, titanium dioxide, zinc oxide, red, yellow, brown and black iron oxides, ferric ammonium ferrocyanide, manganese violet, ultramarine, titaniated mica, bismuth oxychloride and the like. One or more colorants are optionally present in a total amount of about from 0.001% to about 20%, for example about 0.01% to about 10%, or about 0.1% to about 5%.

The compositions of the present invention optionally comprise an active material, which is operable for the prevention or treatment of a physiological disorder or condition or to provide a cosmetic benefit. In various embodiments, the active agent is an "oral care" active agent operable to treat or prevent a disorder or provide a cosmetic benefit within the oral cavity (e.g., to the teeth, gingival or other hard or soft tissue of the oral cavity). Non-limiting examples of oral care actives among those useful herein include anti-tartar agents, anti-plaque agents, antibacterial agents, antimicrobial agents, anti-caries agents, anti-gingivitis agents, anti-viral agents, anti-inflammatory agents, antioxidants, compatible whitening agents, desensitizing agents, occluding agents, vitamins, nutrients, natural extracts and essential oils, compatible enzymes, periodontal actives, breath freshening agents, malodor control agents, salivary stimulants, pH modifying agents, analgesics and combinations and mixtures thereof. Actives among those useful herein are also disclosed in U.S. Pat. Nos. 6,290,933 and 6,685,921, each of these patents is incorporated herein by reference.

The compositions of the invention may include any other substances commonly used in or desirable in oral care compositions, such as antiplaque agents, plaque dispersion agents, antibacterial agents, anti-inflammatory agents, abrasives, whitening agents, enzymes, anticalculus agents, anticaries agents, stannous ion sources, antioxidant agents, saliva stimulating agents, breath freshening agents, $H_2$ antagonists, desensitizing agents, nutrients, The compositions of the present invention are prepared by adding and mixing the ingredients in a suitable vessel, such as a stainless steel tank provided with a mixer. In one embodiment, the composition components are added to the mixing vessel in the following order: liquid ingredients, thickener ingredients, silicone composite and any flavoring, colorant or sweetener. While the exact mixing order is not determinate, it some embodiments the silicone composite be one of the last components added in the multicomponent composition. The ingredients are then mixed to form a homogeneous dispersion/solution.

The present invention provides methods for enhancing anti-attachment properties of an oral surface, such as a tooth surface, using compositions according to the present invention. As used herein, "tooth" or "teeth" refers to natural teeth, dentures, dental plates, fillings, caps, crowns, bridges, dental implants, and the like, and any other hard surfaced dental prosthesis either permanently or temporarily fixed within the oral cavity. As used herein, anti-attachment properties include preventing, interrupting, or at least inhibiting the binding or adhesion or attachment of plaque-forming material, including biologic material, chemicals, microorganisms, bacteria and food products to surfaces of an oral cavity.

Accordingly, the present invention provides methods for inhibiting bacterial attachment to an oral surface, such as a tooth, comprising applying to the surface a safe and effective amount of a silicone composite comprising a silicone compound and a porous cross-linked polymer. In certain embodiments, the methods of this invention prevents or substantially inhibits adherence and attachment of microorganisms that may form a plaque biofilm on the tooth surface. In various embodiments, the present invention provides methods for inhibiting plaque formation. In certain embodiments, such methods comprise administration of a composition of the present invention additionally comprising at least one of an antiplaque agent and a tartar control agent, as discussed above. In various methods, such compositions are used or the treatment or prevention of gingivitis or periodontitis. In various embodiments, such methods comprise applying a composition comprising: a composite comprising an anti-attachment agent and a porous cross-linked polymer; and a non-aqueous carrier comprising a film forming material. The methods of the present invention comprise applying the composite with a suitable oral carrier.

As referred to herein, "applying" refers to any method by which the silicone composite is placed in contact with the oral surface. Such methods, in various embodiments, comprise direct application of a composition comprising the composite by such methods as rinsing, painting, and brushing. In various embodiments, application of the composite comprises the use of an application device which aids in maintaining contact of the composite to the tooth surface for sufficient time so as to afford the anti-attachment benefits.

EXAMPLES

The following examples are illustrative of the present invention and are not to be construed as a limitation of the invention as many variations are possible without departing from its spirit and scope. Non-limiting examples of oral care compositions are made in accordance with the ingredients listed in the table below.

| | Weight % | | | |
|---|---|---|---|---|
| Ingredients | Comparative Example 1 | Example 2 | Example 3 | Example 4 |
| water | 25 | 20 | 15 | 0 |
| glycerin | 22 | 22 | 22 | 28.9 |
| Sodium CMC | 1 | 1 | 1 | 0 |
| tetrasodium pyrophosphate | 0.25 | 0.25 | 0.25 | 2 |
| sodium tripolyphosphate | 0 | 0 | 0 | 3 |
| titanium dioxide | 0 | 0 | 0 | 1 |
| synthetic amorphous silica | 0 | 0 | 0 | 20 |
| Pluraflo L4370 | 0 | 0 | 0 | 15 |
| Pluracare L1220 | 0 | 0 | 0 | 15 |
| sodium monofluorophosphate (MFP) | 0.76 | 0.76 | 0.76 | 1.14 |
| dicalcium phosphate | 48.7 | 38.7 | 43.7 | 0 |
| sodium lauryl sulfate | 1.2 | 1.2 | 1.2 | 1.5 |
| Crystal Blanc flavor | 0.84 | 0.84 | 0.84 | 0 |
| Brite Crystal flavor | 0 | 0 | 0 | 1.2 |
| sodium saccharin | 0.25 | 0.25 | 0.25 | 1.2 |
| 20% silicone adhesive in dimethicone | 0 | 7.7 | 3.4 | 7.7 |
| Polypore ® | 0 | 2.3 | 1.2 | 2.3 |
| Total (%) | 100 | 100 | 100 | 100 |

Comparative Example 1 depicts a typical dentifrice composition without the use of a cross-linked polymer. Examples 2-4 contain a silicone composite created with POLY-PORE™. Example 4 is a non-aqueous composition. The dentifrice compositions are made by a process generally as follows. The CMC and TSPP are dispersed in glycerin, followed by the addition of a CHITOGLYCAN™ solution. Sodium MFP and sodium saccharin are dissolved in water and added to the solution. A silicone adhesive is diluted to 50% of its concentration using dimethicone. A silicone adhesive POLY-PORE™ complex is made by mixing 23% POLY-PORE™ with the diluted silicone adhesive. Dicalcium phosphate is added and uniformly dispersed. The silicone adhesive/POLY-PORE™ complex is added to the solution and homogeneously dispersed, followed by the addition of flavor and sodium lauryl sulfate. Examples 2-4 exhibit greater than a 60% reduction in the bacterial attachment as compared to Example 1. For example, a 1:2 (water:toothpaste) slurry of Example 2 was exposed to a HAP disc and yielded a 75% reduction as compared to a water treated disc.

What is claimed is:

1. An oral care composition comprising a silicon composite and a dentifrice vehicle, wherein the silicon composite consists of a silicone compound sorbed, at an amount of about 50% to about 95% by weight of the composite, onto a porous cross-linked polymer.

2. The composition of claim 1, wherein the polymer comprises at least one polymerized polyunsaturated monomer chosen from acrylate and methacrylate.

3. The composition of claim 1, wherein the polymer comprises polyitaconate.

4. The composition of claim 1, wherein the polymer has a BET pore volume of about 0.1 to about 0.3 cc/g.

5. The composition of claim 1, wherein the silicone composite consists of the silicon compound sorbed, at an amount of about 70% to about 90% by weight of the composite, onto the cross-linked polymer.

6. The composition of claim 1, wherein the silicone compound comprises up to about 40% silicone adhesive in dimethicone.

7. The composition of claim 1 further comprising a carrier.

8. The composition of claim 7, wherein the carrier is a non-aqueous carrier.

9. The composition of claim 7, wherein the carrier comprises a hydrophilic polymer.

10. The composition of claim 9, wherein the hydrophilic polymer is at least one polymer chosen from polyethylene glycols, nonionic polymers of ethylene oxide, block copolymers of ethylene oxide and propylene oxide, carboxymethylene polymers, and polyvinyl pyrrolidone.

11. The composition of claim 7, further comprising at least one active material chosen from anti-tartar agents, anti-plaque agents, and periodontal actives.

12. The composition of claim 7, wherein the polymer comprises at least one polymerized polyunsaturated monomer chosen from acrylate and methacrylate.

13. The composition of claim 7, wherein the polymer comprises polyitaconate.

14. The composition of claim 7, wherein the polymer has a BET pore volume of about 0.1 to about 0.3 cc/g.

15. The composition of claim 7, wherein the silicone composite consists of the silicone compound sorbed, at an amount of about 70% to about 90% by weight of the composite, onto the cross-linked polymer.

16. The composition of claim 7, wherein the silicone compound comprises up to about 40% silicone adhesive in dimethicone.

17. The composition of claim 7, wherein the silicone composite is present in the composition in an amount of about 5 to about 30% by weight.

18. A method comprising applying to oral surface a safe and effective amount of the composition of claim 1.

19. A method comprising applying to an oral surface a safe and effective amount of the composition of claim 7.

20. The method of claim 19, wherein the method does one or more of the following: inhibits bacterial attachment to an oral surface, inhibits plaque formation, prevents gingivitis, treats gingivitis, prevents periodontitis, and treats periodontitis.

* * * * *